(12) United States Patent
Gutierrez et al.

(10) Patent No.: US 6,737,086 B2
(45) Date of Patent: May 18, 2004

(54) BIOLOGICALLY ACTIVE SUBSTANCES, METHOD FOR OBTAINING AND COMPOSITIONS CONTAINING THEM

(75) Inventors: Gilles Gutierrez, Lyons (FR); Mostafa Serrar, Villeurbanne (FR); Lionel Viornery, Lyons (FR); James Norton, Fillongley Hall (GB)

(73) Assignee: INOVAT S.A.R.L. (TN)

( * ) Notice: Subject to any disclaimer, the term of this patent is extended or adjusted under 35 U.S.C. 154(b) by 0 days.

(21) Appl. No.: 10/057,601

(22) Filed: Jan. 25, 2002

(65) Prior Publication Data

US 2002/0102317 A1 Aug. 1, 2002

Related U.S. Application Data

(63) Continuation of application No. 09/331,940, filed as application No. PCT/FR97/02375 on Dec. 22, 1997, now abandoned.

(30) Foreign Application Priority Data

Dec. 27, 1996 (FR) .............................. 96 16116

(51) Int. Cl.[7] ..................... A61K 35/78; A61K 31/74; A61K 47/00
(52) U.S. Cl. .................... 424/767; 424/777; 424/78.03; 424/439; 514/885
(58) Field of Search .............................. 424/767, 78.03, 424/439, 491, 493, 499, 777; 514/2, 844, 885, 886, 887

(56) References Cited

U.S. PATENT DOCUMENTS 3,860,710 A * 1/1975 Sermanni-Giovannozzi et al.
5,747,462 A * 5/1998 Fuentes

FOREIGN PATENT DOCUMENTS

JP 61085324 A * 1/1986
JP 06271452 A * 9/1994

OTHER PUBLICATIONS

Trejo–Gonzales et al., J of Ethnopharm (1996), 55: 27–33. A purified extract from prickly pear catus (*Opuntia fuliginosa*) controls expermentally induced diabetes in rats.*

* cited by examiner

*Primary Examiner*—Christopher R. Tate
*Assistant Examiner*—Michele C. Flood
(74) *Attorney, Agent, or Firm*—Muserlian, Lucas and Mercanti

(57) ABSTRACT

The invention concerns the field of biochemistry, and more precisely biological substances of vegetable origin. The invention concerns substances having non-cytotoxic biological activity, extracted from plants with CAM metabolism, such as plants of the Cactacees, Crassulacees and Saxifragacees family. The invention also concerns the method for obtaining these substances as well as compositions containing them. Said compositions are designed for accelerating and amplifying the synthesis of thermal shock proteins of cells of living beings in vivo or in vitro.

5 Claims, 6 Drawing Sheets

US 6,737,086 B2

Figure 1:
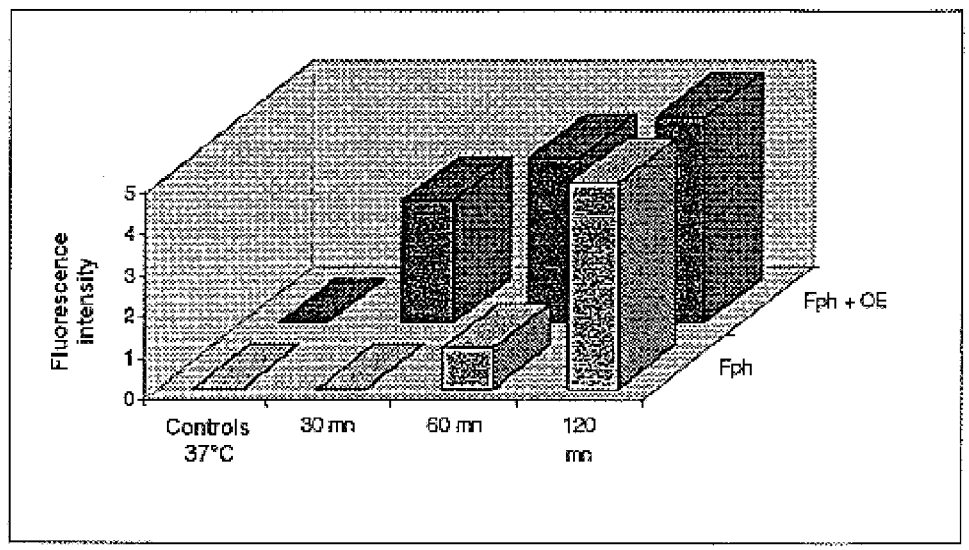

BIOLOGICALLY ACTIVE SUBSTANCES, METHOD FOR OBTAINING AND COMPOSITIONS CONTAINING THEM

PRIOR APPLICATIONS

This application is a Continuation of U.S. patent application Ser. No. 09/331,940 filed Jun. 25, 1999, now abandoned, which is a 371 of PCT/FR97/02375 filed Dec. 22, 1997.

The present invention relates to the biochemical field, and more precisely to biological compounds of vegetable origin.

The present invention relates to new biologically active substances extracted from the fruits of plants with a CAM metabolism, method for obtaining them and pharmaceutical, cosmetic and/or nutritional compositions containing them.

The compositions of the present invention are intended to accelerate and amplify the synthesis of heat shock proteins (or stress proteins) of the cells of living beings. In fact, the stress or aggression conditions are of a nature which alters the quality and synthesis of proteins. Eucaryotes have had to develop metabolic routes intended to preserve their structure.

Plants with a CAM metabolism principally belong to the Cactaceae, Crassulaceae and Saxifragaceae families, which form the only entity capable of developing this type of metabolism.

These plants are particularly adapted to severe climatic conditions and have a particular chlorophyll metabolism which results in a carbon cycle, called CAM ("Crassulaceae Acid Metabolism").

Certain plants are capable of living under stressful conditions (notably plants living in the arid areas of hot or cold deserts or in high-altitude areas), and having a particular metabolism for incorporating $CO^2$, called CAM. Plants of the Cactaceae, Crassulaceae and Saxifragaceae families are well adapted to these heat shock conditions. The synthesis of biological substances which activate or amplify the expression of heat shock proteins is above all abundant in fruit during its formation; the maturation of fruit occurs above all during a period when the temperature returns to normal. The fruit being very exposed to the heat, there is every reason to think that it uses means to protect its protein syntheses.

This protection measure could also be found in other living species.

Among the plants with a CAM metabolism, there can be mentioned in particular the Cactaceae. Cactaceae constitute a family of dicotyledonous plants, commonly called cactus, appreciated for their curious shapes and their brilliantly coloured flowers. One of the most wide-spread genera of the Cactaceae family is constituted by the Opuntias. The *Opuntia ficus-indica* or prickly pear (Cactaceae family) is formed of flat articles, with an oval shape, "flat cactus cladodes", the surfaces of which are sprinkled with areola. Each of these contains a dormant shoot apex, protected by bristles, barbs or glochidia (characteristic of the genus), thorns; they thus constitute the homology of buds. On young shoots, the areola are accompanied by small fleshy leaves, which rapidly fall.

The growth and proliferation of living organisms presumes a high autonomy not only to restore genetic material, guaranteeing the perennity of the species, but also to repair lesions to their body, in order to preserve their integrity. These two necessities require complementary biological systems.

Various mechanisms used by cells to ensure the intact preservation of genetic resources have already been discovered; by way of example, there can be mentioned the protein p 53 system. Similarly, mechanisms exist to ensure the structural conformity of proteins developed from the transcription of information contained in the genome. These synthesis protection mechanisms use various processes and, among these, the synthesis of what are called "heat shock proteins", in spite of the fact that they do not respond in a unique fashion to heat stresses.

The term stress must be taken in its wide sense; it includes stress of various origins, such as temperature rise (from where the name heat shock proteins is derived), oxidizing stress, UV radiation, viral or bacterial infections, or stress resulting from various stimuli such as nutritional deprivation, mechanical aggression or metabolic shock. This is why heat shock proteins are synthesized by the cells to respond to both aggression of a chemical origin (poisons, etc.), of physical origin (ionizing radiation, osmolarity, pH, etc.), of biological origin (cytokines), or mechanical origin.

Heat shock proteins (HSP's) are proteins responsible for protecting the cell, and more particularly its protein syntheses, from aggression of any origin. With age, the capacities for protein synthesis reduce considerably and consequently the ability to respond to aggression is less and less adaptive. This results in the death of numerous cells, lack of protection and a reduction in cell capital, which produces, in particular at the level of mammalian skin, a reduction in the number of keratinocytes available to protect the dermis. Time, exposure to the sun and temperature variations induce aggressions which attack the cells. The skin of the young human adult is particularly well adapted to rapidly respond to aggression as it is capable of synthesizing large quantities of heat shock proteins in order to protect the conformation of the proteins during synthesis. With age, heat shock protein synthesis capacities diminish.

Protection of the skin from the sun is one of the care products in greatest demand by consumers and the most recommended by consultants. Variability in the protective ozone layer, the search for summer warmth, the possibility of travel to the tropics have considerably increased the risk of the appearance of skin disorders resulting from exposure to the sun and thermal aggression. Nowadays, protection against UV and IR radiation exists with different filtering or reflection indices, but there are no products to be applied to the skin to protect it against excessive heat or cold.

The body uses heat shock proteins in order to prevent damage caused by numerous types of aggression: aggressions of external origin (photoluminous, thermal radiation, chemical or biological compounds), but also aggressions of internal origin (hyperthermia, hypothermia, variation in biological parameters, such as for example osmolarity, concentration of certain substances, etc.).

The heat shock proteins are also called stress proteins, shock proteins; scientific terminology refers to them as HSP's. These proteins can also be called, in certain cases, chaperone proteins and, in other cases, glucose regulated proteins (GRP's).

Heat shock proteins (HSP's) include a very large number of molecules. In order to simplify their naming, it is therefore agreed to define them specifically by their molecular weight, expressed in kilodaltons (kDa). Different groups of HSP's can thus be identified: hsp 110's (110 kDa), hsp 90's (90 kDa), hsp 70's (70 kDa) which represent the largest family of hsp's; hsp 60's (60 kDa), hsp 47's (47 kDa) and small hsp's (i.e. between 16 and 40 kDa).

The heat shock proteins constitute a large molecular family involved in maintaining the spatial conformation of proteins. For this reason, when the temperature rises, the spatial structure of proteins is modified (this is the same phenomenon as the coagulation of albumin in an acid medium).

The large number of HSP's results from the fact that they act with a specificity which depends on the cell type, their destination or also the type of stress. Each member of the HSP family thus has a quite precise function and the intervention points are very numerous. The HSP's apply not only to the post-translational stages forming part of a normal synthesis function and of the proteins' life, such as the setting up of the conformation and their transport, but also at the level of the events which alter protein synthesis by intervening in the selection of metabolic routes: restoration, destruction and elimination of modified substrates. Certain HSP's have an action which develops during thermal aggression, others only play their roles in the presence of a chemical risk.

There is therefore a large number of shock proteins, each adapted to a specific protection mechanism.

These substances, of protein type, are coded by genes for which the chromosome location has only been established for a few of these. It should be noted that these substances are maintained in their state in a totally constant manner throughout the phylogeny both in terms of the sequence and in terms of the function, which means that the consequences of stimulation or modifications in synthesis are found not only with human cells but probably with the cells of all animal species.

Although the HSP 70's are synthesized in a constitutive manner, in order to resist aggressions, where necessary, the cells synthesize large quantities of these proteins. It is therefore possible to treat cells with these protein substances in order to enhance their viability in the event of stress. It is therefore possible to intervene on the improvement of cell viability by adding substances either to the nutritive medium or into the heart of the cells themselves. Their action has been studied, thanks to genetic engineering or molecular biology, by vectorizing the genes coding for the HSP's.

Addition techniques have numerous disadvantages for multi-cellular organisms:
it is not possible to target the cells concerned,
the substance can be destroyed in extracellular media,
it is not possible to bring a protein to numerous cells.

Molecular biology techniques also have major drawbacks:
the very large number of HSP's and their specificity render operations sensitive, numerous and tedious,
amplification of the coding genome short-circuits regulations,
it is not currently possible to control synthesis of the protein,
during gene transfection, the protein is always overexpressed whatever the circumstances.

Production of HSP's by induction of transcription (synthesis of mRNA's from DNA) or of translation (synthesis of proteins by ribosomes from mRNA's) is possible if pharmacological substances are available which act either at the level of the plasma membrane, or in the cytoplasm, or also at the level of the nucleus.

In plants with a CAM metabolism, and more particularly in the fruit of plants of the Cactaceae family, the Applicant has found substances which may protect protein syntheses. After various research, it was discovered, surprisingly, that the substances were recognized by animal cells.

A subject of the present invention is new biologically active substances, in particular on the metabolism of HSP's, non cytotoxic, isolated from plants with a CAM metabolism, such as plants of the Cactaceae, Crassulaceae and Saxifragaceae family.

The present invention relates in particular to substances obtained from the skin of fruit of the Cactaceae family, and more precisely from the skin of Opuntia fruits, and in particular from that of the prickly pear fruit.

The process for obtaining non-cytotoxic biologically active substances is characterized in that a fruit of a plant with a CAM metabolism is subjected to drying, then to dehydration, followed by leaching with a polar organic solvent in order to obtain an organic fruit extract, this extract is diluted with water, the diluted extract is purified by leaching with hexane, the hexanic organic fraction is separated off then evaporated to dryness under vacuum, and the active fraction of the fruit of the plant with a CAM metabolism is obtained, i.e. that containing said biologically active substances. The active fraction is further dried, and optionally taken up in a biocompatible solvent such as ethanol, or with an appropriate solvent according to the desired operations.

Any part of the plant with a CAM metabolism can be used; the fruit of the plant is preferably used, and in particular the skin of fruits of plants of the Cactaceae family. The fruit of the plant with a CAM metabolism is a fruit of the plant of the Cactaceae family, and in particular the Opuntia fruit, and specifically the prickly pear fruit.

The process for obtaining the active substance(s) is further characterized by the fact that the skin of mature or immature fruit can be used; the fruit skin is obtained by peeling, erosion or grinding of the fruit.

The polar organic solvent used in the obtention process is preferably a solvent chosen from the aliphatic alcohols and the aliphatic ketones which are miscible with water such as ethanol and/or acetone. Direct extraction from the plant with a slightly polar or non-polar solvent can also be an alternative which comprises putting in contact with a polar solvent.

The biologically active substances according to the invention, non cytotoxic, extracted from plants with a CAM metabolism such as plants of the Cactaceae, Crassulaceae and Saxifragaceae families, and in particular those extracted from the skin of Opuntia fruits, and specifically, that of the prickly pear fruit, display very useful pharmacological properties, in particular on the metabolism of HSP's, and can therefore be used therapeutically, in cosmetics and/or in foodstuffs.

These non cytotoxic substances, extracted from plants with a CAM metabolism such as Cactaceae, Crassulaceae, Saxifragaceae act on the cells of tissues or of living beings by accelerating and/or amplifying the synthesis of heat shock proteins (HSP's), when the cell is subjected to stress or to various aggressions involving the synthesis of heat shock proteins.

It is important to emphasize the non-cytotoxicity of these substances, as most cytotoxic substances induce an increase in the synthesis of heat shock proteins (HSP's).

The substances of the present invention are intended to treat the cells of tissues or of living beings, in order to improve their resistance to stress or to various aggressions which cause the synthesis of heat shock proteins, or to prevent and/or treat the consequences of stress or of various aggressions which cause the synthesis of heat shock proteins and which modify the synthesis of proteins.

Generally, the substances of the present invention are intended to prevent and/or treat any consequence of a symptom resulting in stress or a cell aggression.

These substances are used over a very wide therapeutic, cosmetic and/or nutritional field.

Thus, the substances of the present invention can be used in the prevention and/or treatment of the consequences of vascular ischemias; cutaneous fibroses (keloids), pulmonary and hepatic fibroses; surgical operations (side effects due to treatments by chemotherapy, ionizing radiation or radiotherapy, etc.), the menopause; aggression by free radicals; mechanical lesions: stretching of a muscle or of the skin (atrophia striata et maculosa); mechanical friction (horses, harnesses, shoes, clothes, etc.); thermal and photon radiation; the prevention of risks linked to the therapeutic activity, to the complication of certain diseases (viral hepatites, cancers, various infections, degenerative diseases involving an apoptotic phenomenon), to certain professional human activities such as those of firemen or workers liable to be subjected to ionizing radiation such as underwater and other diving, etc.

For these purposes, one or more substances according to the invention, isolated from the skin of the fruit of plants with a CAM metabolism such as the plants of the Cactaceae, Crassulaceae, Saxifragaceae family, and in particular the skin of Opuntia fruits, and specifically the prickly pear fruit, are used on their own or in combination or as a mixture with one or more active ingredients having a complementary action as well as with a non-toxic excipient or inert vehicle appropriate for the use envisaged, with a view to producing pharmaceutical, cosmetic and/or nutritional compositions.

The present invention further relates to the use of a substance or biologically active substances in order to accelerate and amplify the synthesis of heat shock proteins (HSP's) in cell culture media.

The compositions according to the invention are intended for administration by digestive, parenteral, topical or rectal route. The compositions are thus presented in the form of plain, coated or sugar-coated tablets, capsules, gelules, pills, cachets, syrups, powders to be ingested or for external use, adjuvant compositions for post-operative cicatrization, burns or traumatisms; suppositories; injectable solutes or suspensions, packaged in ampoules; creams, gels or ointment.

Complementary active ingredients suitable for such administrations and for such compositions are for example sun filters, antiseptics, antibiotics, analgesics, etc.

Excipients which are suitable for such administrations and for such compositions are production adjuvants (binding agents, fluidizing agents, etc.), sapidity agents, colouring agents and stabilizers, etc.

For therapeutic, cosmetic and/or nutritional use, the quantity of active ingredient (i.e. the biologically active substances according to the invention) ranges, in equivalents of dry plants, from $10.10^{-3}$ mg/ml to 400 mg/ml, in particular from 0.1 mg/ml to 200 mg/ml, and preferably from 0.5 mg/ml to 100 mg/ml per unit dose.

The daily dosage ranges from 0.1 mg/kg to 200 mg/kg per day, depending on the therapeutic, cosmetic and/or nutritional indication and the administration route.

As the plant and the dry extract are not toxic, the upper limit of the dose administered is only limited by ingestion capacity, solubility, biological and pharmacological availability or also the effect associated with at least one other active ingredient present in the plant independently of the active fraction.

The following examples illustrate the invention without however limiting it. These examples are described with reference to the attached figures.

EXAMPLE I
Amplification of the Synthesis of HSP 90 of Fibroblasts Subjected to Thermal Treatment.

Heat shock proteins (HSP's) are essential to the preservation of protein synthesis during external aggression. The increase in HSP synthesis allows better protection of the cell, for example on the occasion of an increase in temperature.

In the context of the experiment described below, substances were sought which were capable of amplifying the synthesis of HSP 90 when the temperature was increased to 43° C. without inducing synthesis of this molecule at 37° C. (normal condition) in order to eliminate the induction of any production of HSP by a toxic substance.

The substance studied below originates from an alcoholic extract obtained from the skin of *Opuntia ficus-indica* fruits or prickly pear fruits. This substance is hereafter referred to as "OE", meaning "Opuntia Extract".

In order to achieve this, 100 g of dehydrated plant or dehydrated whole fruit or also 1 g of dehydrated fruit skin was treated with 10 times its weight of polar organic solvent. 10 μl of the extract obtained was added to 1 ml of medium appropriate for the culture of keratinocytes or fibroblasts. After incubation overnight at 37° C., synthesis of the HSP's is not modified, but after exposure to a temperature of 43° C., the HSP's appear much earlier.

As an example, HSP 90 revealed by indirect immunofluorescence appears between 10 and 20 minutes in a culture of fibroblasts incubated in the presence of an extract of Cactaceae (O.E.) while the culture media containing unincubated cells only show HSP 90 one or two hours later.

The values in the tables and graphs 1, 2, 3 and 4 are expressed in arbitrary units as a function of the fluorescence surface area for a threshold determined for all the observations. These are relative values in arbitrary units established according to a detection threshold which is identical for all the observations using a Biocom apparatus, and by calculating the fluorescence ranges revealed by an antibody combined with fluorescein and directed against the specific HSP antibody.

TABLE I

Synthesis of HSP 90 by fibroblasts of human skin in culture at 43° C.

|  | Control 37° C. | 30 mins. | 60 mins. | 120 mins. |
| --- | --- | --- | --- | --- |
| Hsf | 0 | 0 | 1 | 5 |
| Hsf + OE | 0 | 3 | 4 | 5 |

Hsf = Human skin fibroblasts

Opuntia extract, added at a dose of 1% to the culture medium, expresses no activity after incubation overnight at 37° C., while the same human skin fibroblasts cultured at a temperature of 43° C., in the presence of an Opuntia extract, cause the more rapid appearance of HSP 90.

The presence of Opuntia extract (OE) in the culture medium thus allows the activation of the HSP 90 synthesis process with respect to that developed by the untreated cell. Synthesis is not amplified, but is activated more rapidly. Instead of beginning normally after 120 mins., synthesis of the HSP 90 by fibroblasts in the presence of OE begins at 30 minutes after the temperature is raised to 43° C. (cf. FIG. 1).

During thermal aggression, OE allows improved preservation of cell material due to the rapid triggering of the HSP synthesis process.

During another experiment, it was possible to specify that the appearance of HSP 90 by fibroblasts of human skin taken from a surgical explant originating from a 5-year-old subject, subjected to a thermal stress of 43° C., occurs at between 10 and 20 minutes, while cells originating from the same child but not treated with Cactaceae extract only show HSP 90 after 60 mins.

The groups of data appearing in the 3 tables are independent of each other and cannot therefore be compared.

TABLE II

Synthesis of HSP 90 by fibroblasts

|  | Untreated | Treated with OE |
| --- | --- | --- |
| $T_0$ | 1 | 1 |
| 10 mins. | 1 | 1 |

TABLE II-continued

Synthesis of HSP 90 by fibroblasts

|  | Untreated | Treated with OE |
|---|---|---|
| 20 mins. | 1 | 2.5 |
| 30 mins. | 1 | 5 |

Figure 2:
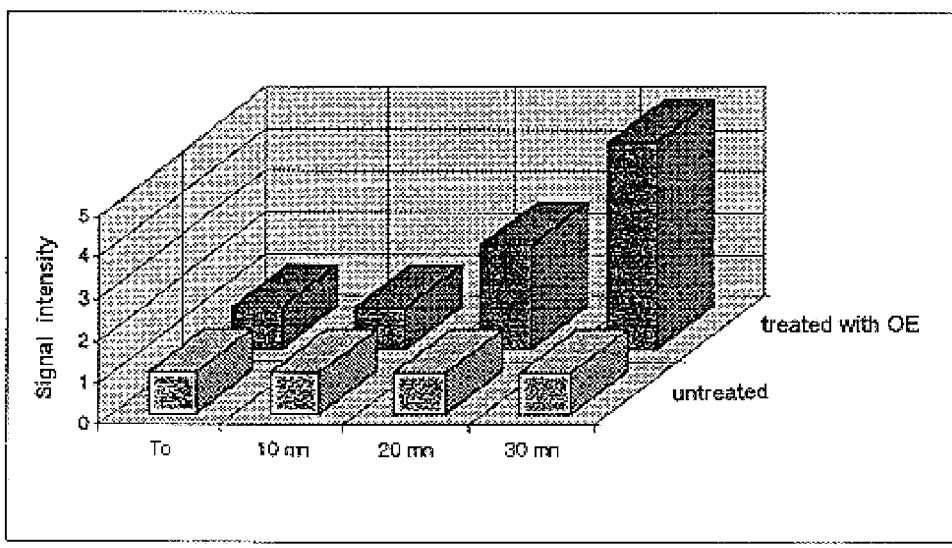

Table II is illustrated by FIG. 2.

EXAMPLE II

Synthesis of Heat Shock Proteins (HSP's) by Human Epithelial Cells

TABLE III

Synthesis of HSP 90 by keratinocytes

|  | Untreated | Treated with OE |
|---|---|---|
| $T_0$ | 1 | 1 |
| 30 mins. | 1 | 4 |
| 60 mins. | 1 | 5 |
| 120 mins. | 4 | 5 |

Figure 3:
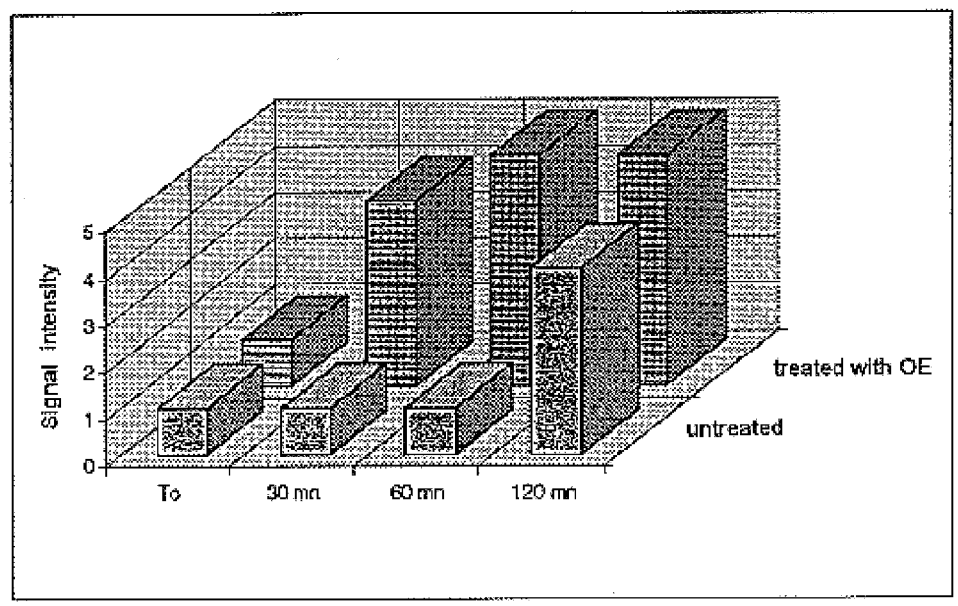

Table III is illustrated by FIG. 3.

TABLE IV

Synthesis of HSP 27 by keratinocytes

|  | Untreated | Treated with OE |
|---|---|---|
| $T_0$ | 1 | 1 |
| 30 mins. | 1 | 5 |
| 60 mins. | 2 | 5 |
| 120 mins. | 4 | 5 |

Figure 4:
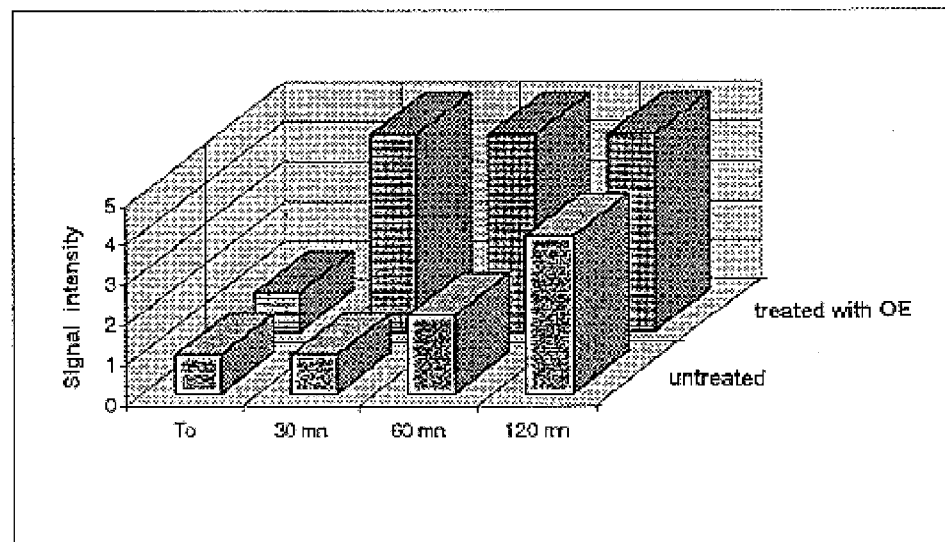

Table IV is illustrated by FIG. 4.

EXAMPLE III

Study of the Cytocompatibility of the Opuntia Extract

The extract of plants having the CAM metabolism must be non-cytotoxic in order to avoid inducing HSP synthesis due to its toxicity. The cytocompatibility studies were carried out on fibroblasts and keratinocytes. Two types of test were carried out: mitochondrial activity and cell proliferation. Mitochondrial activity is evaluated by the XTT test.

The XTT test is a calorimetric test based on the reduction of a soluble tetrazolium salt (XTT=2,3-bis[2-Methoxy-4-nitro-5-sulphophenyl]-2H-tetrazolium-5-carboxanilide), (if the derivative is insoluble: MTT test=[3-(4,5-dimethyl thiazol-2-yl)-2,5-diphenyl-2H-tetrazolium bromide], by mitochondrial NADPH reductase in a colouring agent of blue violet formazan type.

For example, $2.10^4$ cells are cultured in a standard manner and treated with various concentrations of the active product to be tested. Readings are taken at 24 hours or at 48 hours.

The XTT test gives a value for mitochondrial activity, a value given in optical density (O.D.) at the wavelength associated with formazan blue.

Cell proliferation is carried out by a cell count using a cell counter. It is expressed in number of cells.

A) Test on Fibroblasts:

The fibroblasts originate from an explant of human skin taken from a 3-year-old child (third passage cells).

TABLE V

Study of the metabolism of fibroblasts cultured in the presence of Opuntia extract.

|  |  |  |  | Average (O.D.) | Standard deviation |
|---|---|---|---|---|---|
| Control | 0.314 | 0.368 | 0.479 | 0.387 | 0.069 |
| OE 5% | 0.309 | 0.364 | 0.361 | 0.345 | 0.025 |
| OE 2% | 0.314 | 0.415 | 0.428 | 0.386 | 0.051 |
| OE 1% | 0.312 | 0.522 | 0.585 | 0.473 | 0.117 |
| OE 0.5% | 0.320 | 0.405 | 0.354 | 0.360 | 0.035 |
| OE 0.2% | 0.300 | 0.318 | 0.330 | 0.316 | 0.012 |
| OE 0.1% | 0.247 | 0.287 | 0.327 | 0.287 | 0.033 |
| OE 0.05% | 0.230 | 0.249 | 0.281 | 0.253 | 0.021 |

The Opunia extract does not modify the fibroblasts' metabolism: the values are not statistically significant with respect to the control.

Figure 5:
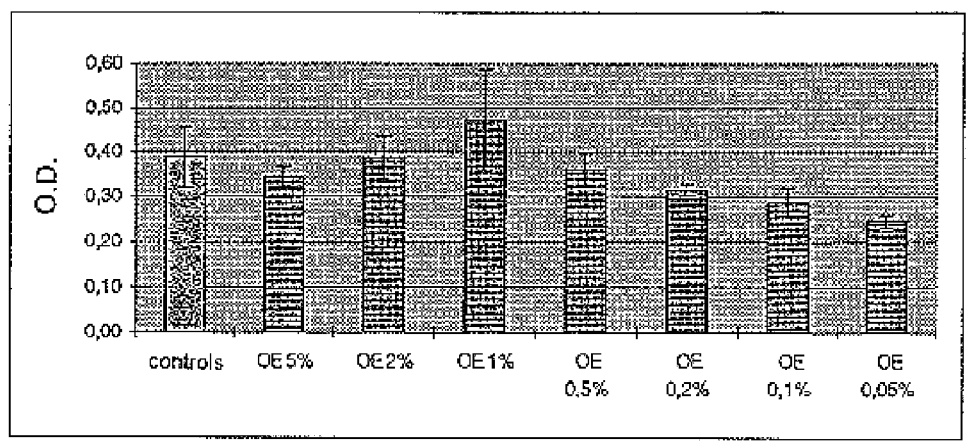

Table V is illustrated by FIG. 5.

TABLE VI

Effect of CAM metabolism plant extracts on fibroblast proliferation. Seeding $10^4$ cells.

|  | Value in thousands of cells |
|---|---|
| Control | 255 |
| OE 5.00% | 281 |
| OE 2.00% | 215 |
| OE 1.00% | 260 |
| OE 0.50% | 251 |
| OE 0.20% | 225 |
| OE 0.10% | 252 |
| OE 0.05% | 257 |

The Opuntia extract does not modify the fibroblast proliferation after two days of incubation.

Figure 6:
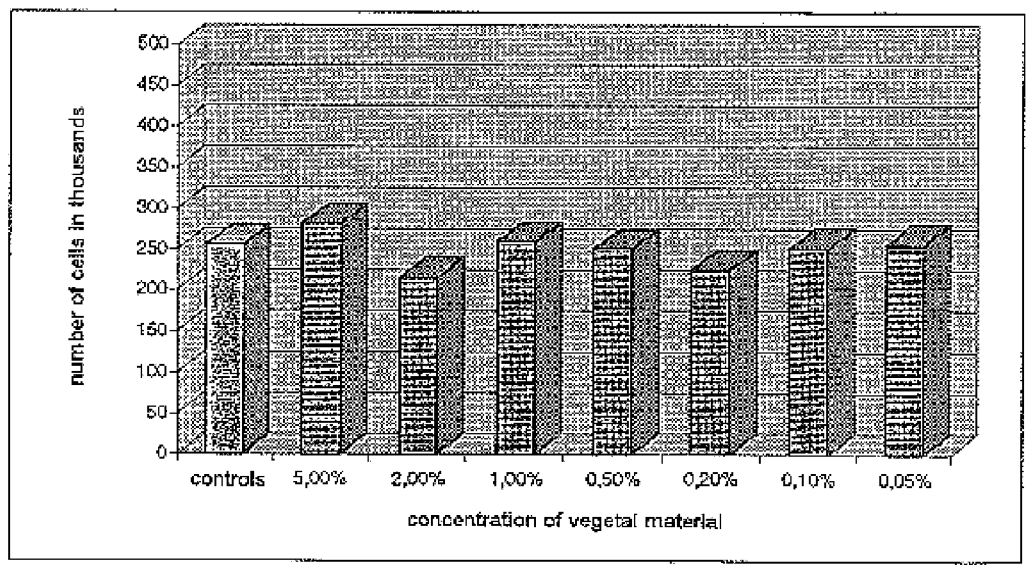

Table VI is illustrated by FIG. 6.

B) Test on Keratinocytes

The keratinocytes originate from a human skin explant originating from the prepuces of 2-year-old children.

TABLE VII

Study of the mitochondrial metabolism of human keratinocytes cultured in the presence of Opuntia extract

|  |  |  |  | Average (O.D.) | Standard deviation |
|---|---|---|---|---|---|
| Control 37° C. | 0.948 | 1.182 | 1.139 | 1.090 | 0.125 |
| OE 0.05% | 1.151 | 1.169 | 1.235 | 1.185 | 0.044 |
| OE 0.1% | 0.940 | 0.984 | 1.006 | 0.977 | 034 |
| OE 0.2% | 1.003 | 1.130 | 1.096 | 1.076 | 0.066 |
| OE 0.5% | 1.098 | 1.217 | 1.225 | 1.180 | 0.071 |
| OE 1.0% | 1.057 | 1.204 | 1.402 | 1.221 | 0.173 |
| OE 2.0% | 1.185 | 1.305 | 1.297 | 1.262 | 0.067 |
| OE 5.0% | 1.180 | 1.243 | 1.180 | 1.201 | 0.036 |

The Opuntia extract is cytocompatible with keratinocytes.

No statistically significant variation is observed in the mitochondrial activity of the keratinocytes cultured with concentrations of Opuntia extract varying from 0.05% to 5%.

Figure 7:
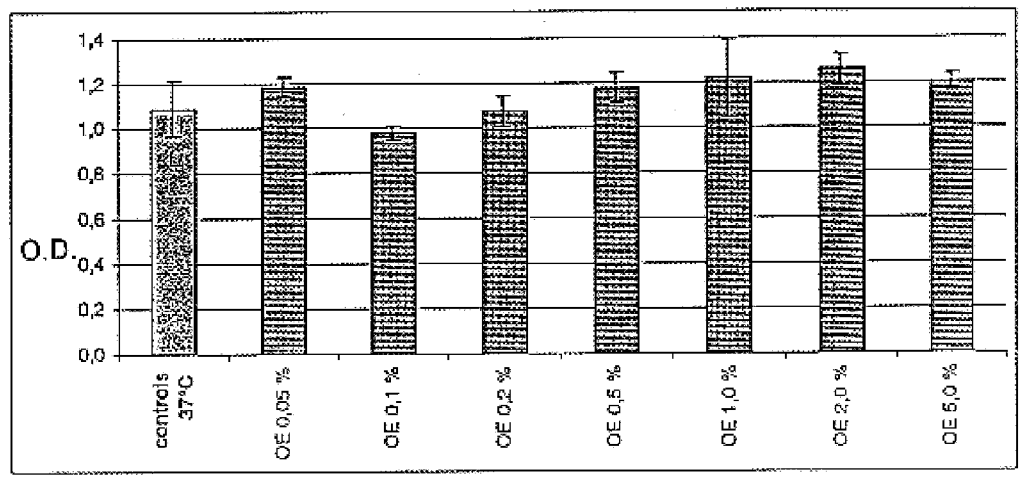

Table VII is illustrated by FIG. 7.

TABLE VIII

Proliferation of keratinocytes in thousands of cells

| | Value in thousands of cells |
|---|---|
| Control | 82,300 |
| OE 5% | 114,600 |
| OE 2% | 86,300 |
| OE 1% | 102,300 |
| OE 0.50% | 82,600 |
| OE 0.20% | 82,500 |
| OE 0.10% | 82,300 |
| OE 0.05% | 81,900 |

The Opuntia extract does not modify the proliferation of keratinocytes.

Figure 8:
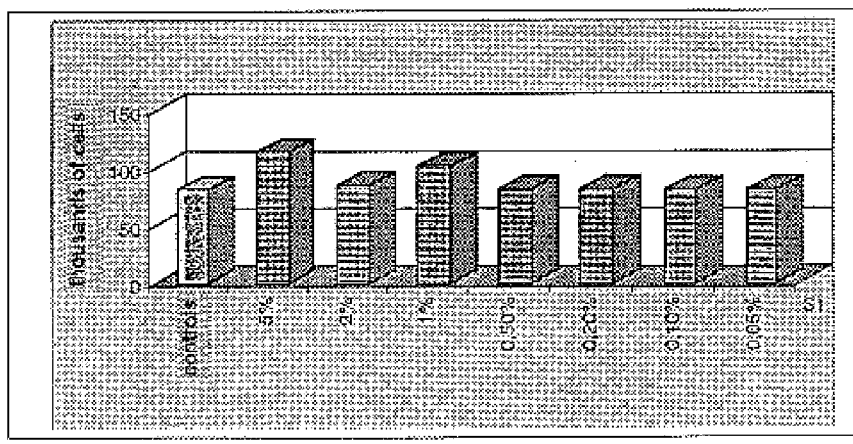

Table VIII is illustrated by FIG. 8.

EXAMPLE IV

Study of the Influence of Various Doses of CAM Metabolism Plant Extract on the Viability of Keratinocytes Subjected to Thermal Treatment at 48° C. for one Hour.

After contact with the Opuntia extract for 30 minutes, the keratinocytes are incubated at 48° C. for one hour.

The viability of the cells is evaluated by the XTT test.

TABLE IX

Mitochondrial activity of keratinocytes by Opuntia extract and treated at 48° C.

| | | | | | | | Average (O.D.) | Standard deviation |
|---|---|---|---|---|---|---|---|---|
| Control 37° C. | 0.199 | 0.198 | 0.198 | 0.195 | 0.195 | 0.198 | 0.197 | 0.002 |
| Control 48° C. (*) | 0.104 | 0.101 | 0.102 | 0.097 | 0.100 | 0.101 | 0.101 | 0.002 |
| Krc 48° C. + 0.1% OE | 0.123 | 0.129 | 0.128 | 0.126 | 0.127 | 0.122 | 0.126 | 0.003 |
| Krc 48° C. + 0.5% OE | 0.152 | 0.155 | 0.115 | 0.156 | 0.153 | 0.149 | 0.147 | 0.016 |
| Krc 48° C. + 1.0% OE | 0.178 | 0.182 | 0.178 | 0.178 | 0.179 | 0.177 | 0.179 | 0.002 |

(*): untreated
Krc: keratinocytes

Figure 9:
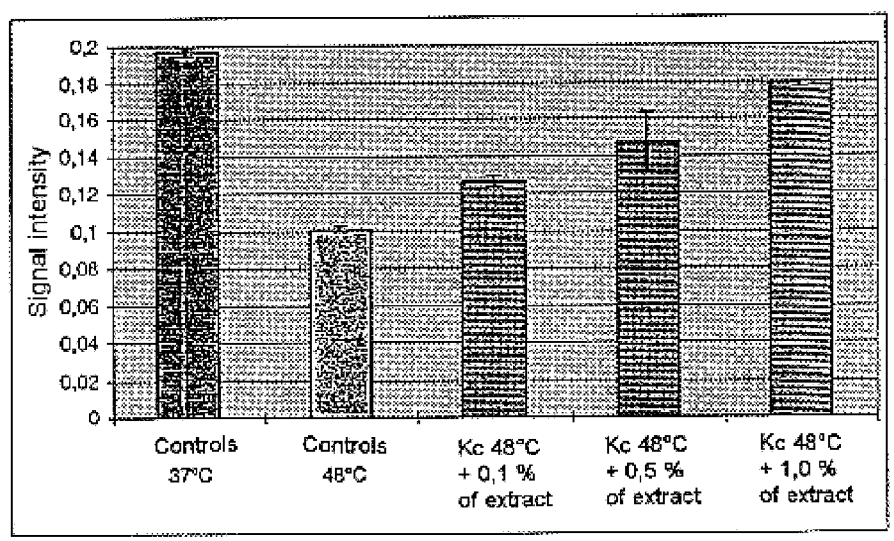

Table IX is illustrated by FIG. 9.

The thermoprotective effect is dose-dependent and appears with the use of 10 (1 per 1 ml culture well obtained by the maceration of 1 g of plants in 10 ml of polar anhydrous organic solvent.

EXAMPLE V

Thermoprotective Effect of CAM Metabolism Plant Extracts. Study of the Viability of Cells Treated with Opuntia Extracts Obtained with the Different Parts of the Plant.

The conditions of the XTT test on fibroblasts of human skin are as follows:

Incubated overnight at 37° C. with or without OE (heat shock control)
First heat shock for 20 mins. at 48° C.
Incubation for 40 mins. at 37° C. (production of HSP)
Second shock for 20 mins. at 50° C.
15 mins. at 37° C.
XTT test for 3 hours at 37° C.

TABLE X

Study of the resistance of fibroblasts to heat shocks when they are treated by the fruit skin extract

| | | | | | | Average (O.D.) | Standard deviation |
|---|---|---|---|---|---|---|---|
| Control (37° C.) | 0.630 | 0.771 | 0.564 | 0.646 | 0.911 | 0.704 | 0.138 |
| Heat shock control | 0.688 | 0.696 | 0.701 | 0.611 | 0.671 | 0.673 | 0.037 |
| Solvent + shock | 0.523 | 0.700 | 0.717 | 0.713 | 0.671 | 0.665 | 0.081 |
| 1 = juice | 0.587 | 0.688 | 0.818 | 0.764 | 0.681 | 0.708 | 0.088 |
| 2 = pulp | 0.592 | 0.717 | 0.719 | 0.712 | 0.687 | 0.685 | 0.054 |
| 3 = skin | 0.782 | 0.929 | 0.899 | 1.057 | 0.891 | 0.911 | 0.598 |
| 1 + 2 + 3 | 0.748 | 0.788 | 0.627 | 0.772 | 0.752 | 0.737 | 0.064 |

The control at 37° C. is cultured on another plate.

The optical densities (O.D.'s) measured during the XTT test on the fruit skins are statistically significant with respect to all the other average optical densities except in the case of the total solution (1+2+3).

This shows that for certain Cactaceae the full effect is contained within the skin.

Fibroblasts resist heat shock better when they are treated with the extract of the fruit skin.

Figure 10:
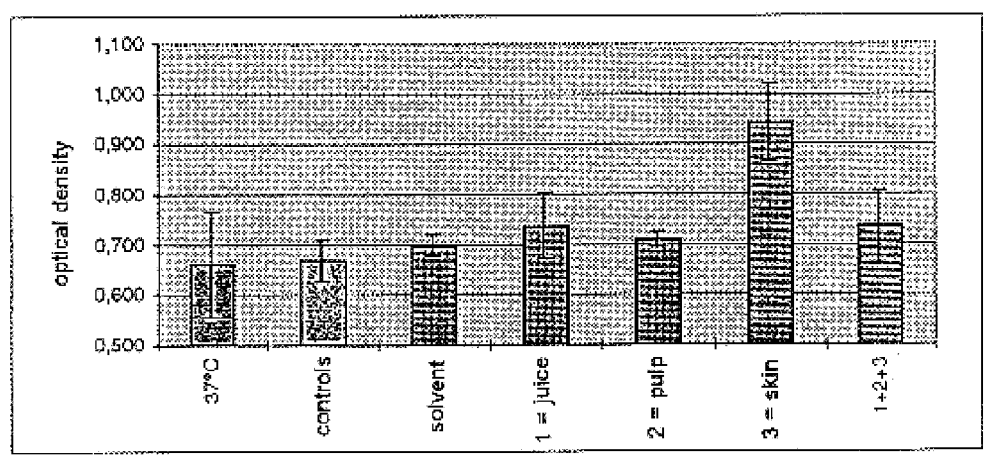

Table X is illustrated by FIG. 10.

EXAMPLE VI

Study of the Viability of Cells Treated with Opuntia Extracts Obtained with the Different Parts of Fruit.

TABLE XI

This illustrates the comparison with the control.

| | 37° C. | Shock | Solvent |
|---|---|---|---|
| Reference (37° C.) | | −0.070 | −0.100 |
| Heat shock control | 0.010 | 0.000 | −0.700 |
| Solvent + shock | 0.040 | 0.030 | 0.000 |
| 1 = juice | 0.078 | 0.068 | 0.038 |
| 2 = pulp | 0.049 | 0.039 | 0.009 |
| 3 = skin | 0.283 | 0.273 | 0.243 |
| 1 + 2 + 3 | 0.075 | 0.065 | 0.035 |

The fibroblasts resist heat shocks better when they are treated with the fruit skin extract.

Figure 11:
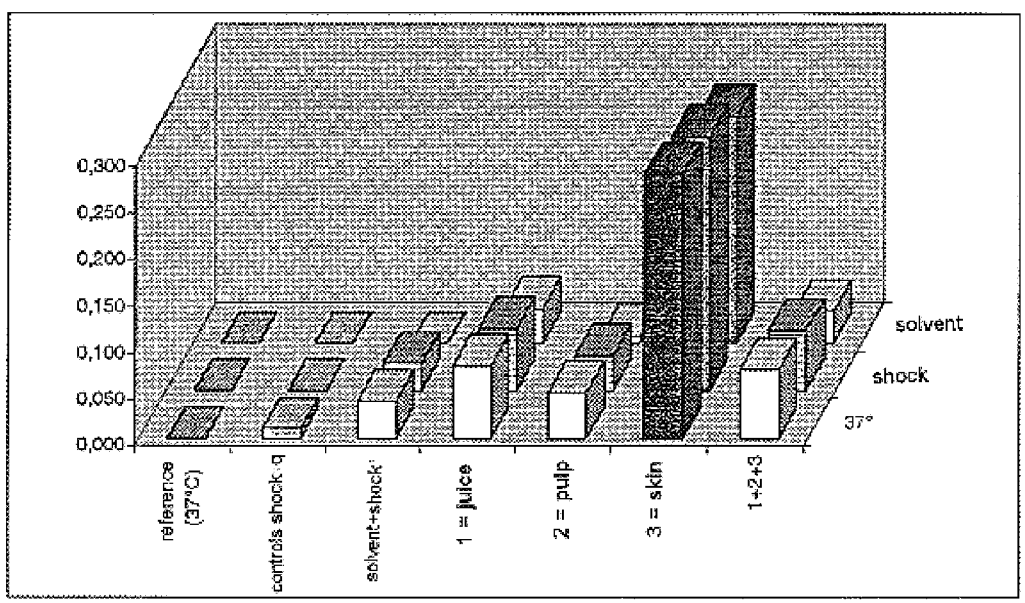

Table XI is illustrated by FIG. 11.

What is claimed is:

1. A method for improving the resistance to stress or aggression connected with the synthesis of heat shock proteins (HSP) in humans or in animals, comprising administering an effective amount of an alcoholic extract obtained from dehydrated skin of a plant which exhibits Crassulacean acid metabolism (CAM) to said humans or animals sufficient to improve said resistance; whereby the alcoholic extract accelerates or amplifies the synthesis of the heat shock proteins.

2. A method of claim 1 wherein said plant is a fruit of Opuntia.

3. A method of claim 1 wherein said plant is obtained from the skin of fruits of *Opuntia fiscus-indica*.

4. A method of claim 1 further comprising an inert carrier or vehicle suitable for administration through digestive, parenteral, topical or rectal way is used.

5. A method of claim 1 wherein the effective amount of said alcoholic extract ranges from $10 \times 10^{-3}$ mg/ml to 400 mg/ml per unit dosage.

* * * * *